United States Patent [19]

Ricketts

[11] Patent Number: 5,534,266
[45] Date of Patent: Jul. 9, 1996

[54] BOVINE TEAT DIP

[75] Inventor: David J. Ricketts, Irvine, Calif.

[73] Assignee: Devtech Corporation, Irvine, Calif.

[21] Appl. No.: 262,774

[22] Filed: Jun. 20, 1994

[51] Int. Cl.$^6$ .......................... A61K 33/36; A61K 31/19; A61K 31/045

[52] U.S. Cl. .......................... 424/672; 514/571; 514/738

[58] Field of Search ............................. 424/672; 514/571, 514/738

[56] References Cited

U.S. PATENT DOCUMENTS 4,466,959  8/1984  Lauermann et al. ..................... 424/150

OTHER PUBLICATIONS

Chemical Abstract, 117:55818 (1992). Boddie et al.

*Primary Examiner*—Zohreh Fay
*Attorney, Agent, or Firm*—Willie Krawitz

[57] ABSTRACT

An iodophor teat dip is disclosed comprising a solution of a fatty alcohol polyglycol ether carboxylic acid, glycerin, $I_2$, I- (or HI) and, a pH buffer. The teat dip reduces the spread of mastitis infection, imparts a smoother teat condition, improves milk let down, and has few discernible long term effects.

22 Claims, No Drawings

5,534,266

BOVINE TEAT DIP

BACKGROUND OF THE INVENTION

This invention relates to a new and improved iodophor teat dip containing $I_2$ and I- (or HI), and glycerin which is suitable for reducing the spread of mastitis infection, and improving teat appearance and skin condition; this in turn enables faster let down and milk out.

Many types of teat dip similar formulations have been employed in the past, and typical examples are found in U.S. Pat. Nos. 2,977,315; 3,950,554; 4,049,830 4,258,056; 4,371, 517; 4,671,958; 4,678,668; 4,940,702; 5,028,427; 5,175, 160; 5,208,257; and, German Patent 2,936,934.

The use of $I_2$ with I- (or HI) which complexes, rather than reacts with the surfactant to produce unwanted and possibly toxic reaction products, is disclosed in U.S. Pat. Nos. 2,599,140; 2,710,277 and 2,977,315 which describe tamed iodine or iodophor, etc. Also, the use of polyethenoxy detergents and $I_2$ is disclosed in an article by Benjamin Carroll in the Journal of Bacteriology, 69; 413–417, (1955). In an attempt to avoid the use of $I_2$ and I- (or HI), the use of bromo-nitro-propanol as the germicide in teat dips is disclosed in U.S. Pat. No. 4,049,830, but this latter formulation is considered to have insufficient germicidal properties compared to using iodine.

Consequently, present commercial teat dip formulations have been developed with the intent of combining desired germicidal properties with suitable emolliency, and include surfactants such as 9–12 mole ethoxylated phenols containing $I_2$, I- and glycerine. A surfactant of this type employed in a teat dip is sold by Norman Fox & Co. under the trade name of NORFOX N-P9, and listed in "McCutcheon's Emulsifiers and Detergents", 1989 specifically for use with iodophors.

However, the NORFOX N-P9 formulation tends to cause the teat skin to become chapped, cracked and calloused, which in turn leads to infection, which can provide a mastitis site, and weaken the cow for other infections, delayed milk let down, and bovine discomfort when milking.

Another type of teat dip is sold as Klenzade™ Teat Guard, and contains a nonyl phenoxypolyethoxy ethanol surfactant having 1% titratable iodine, but this product does not keep the teat skin soft.

Still other bovine teat dip formulations have employed an emollient such as lanolin, but these formulations have failed to exhibit the desired characteristics of emolliency.

A bovine teat dip formulation is desired which has a suitable capability for dispersing $I_2$ and I- (or HI); does not form toxic or objectionable compounds with $I_2$; improves the teat appearance; reduces teat callousing and cracking; improves milk let down; reduces discomfort when milking; maintains a suitable capability for reducing the spread of mastitis; has a reasonably good phase stable shelf life over a reasonably wide temperature range; and, is inexpensive to formulate.

THE INVENTION

According to the invention, an iodophor teat dip formulation is provided comprising an emulsifier/dispersant of water soluble, nonionic, fatty alcohol polyglycol ether carboxylic acids; glycerin, and the like; effective amounts of $I_2$ and I- (or HI, and the like); and a pH buffer. A suitable emulsifier/dispersant of this type is sold by Alcolac Inc. under the trade names of AKYPO™RLM-45, AKYPO™RLM-100, AKYPO™RLM-130 and AKYPO™RLM-160, and mixtures thereof, the preferred composition being AKYPO™RLM-100 (Chemical Abstracts Registry 74349-89-6).

As described in "McCutcheon's Emulsifiers & Detergents", 1989, these AKYPO™RLM emulsifiers/dispersants are listed for personal care products to improve skin feel, in high electrolyte household and industrial formulae, and as an emulsifier for synthetic latex, but they are not listed for use in teat dip formulations. The entire contents of "McCutcheon's Emulsifiers & Detergents" 1989–1994 are incorporated herein by reference.

However, according to the invention, it has been discovered unexpectedly, that when used in conjunction with appropriate concentrations of glycerin, an iodophor such as $I_2$, I- (or HI) and, a pH buffer, these water soluble, emulsifiers/dispersants produce a teat dip having the above requisite properties. An adequate, liquid phase stable life over a wide range of ambient temperatures is obtained, and moreover, the emulsifier/dispersant complexes the iodine and maintains the iodine in solution, thereby preventing the iodine from precipitating and forming a separate, solid phase. Also, the emulsifier/dispersants function together with the glycerine to impart the necessary emolliency for smooth teats, with reduced cracking, callousing and sores. In turn, this lessens the possibility of infection sites leading to mastitis, and other diseases.

The AKYPO™RLM emulsifiers/dispersants used in the formulation have a range of laureth (11–17) carboxylic acids, with an HLB (Hydrophilic/Lipophilic Balance) number between about 10–16, and the AKYPO™RLM-100 itself has an HLB of 14.8.

Typical formulations comprise $I_2$: about 0.45%–1.3%; HI, or equivalent (e.g., KI, NaI, $CaI_2$, etc., and mixtures thereof): sufficient to form about 0.25%–0.3% I-; glycerin, and the like: about 5%–12.5%; a buffer such as citric acid and/or lactic acid; and, caustic for adjusting the pH to about 4.0–5.5, and preferably to a pH of about 4.8–5.2; emulsifier/dispersant: about 7.5%–12.5%; and, water: balance, all parts by weight.

If the glycerin content is below about 5%, the formulation did not appear effective. Other hydroxy equivalents to glycerine may be employed, and include: glycerine; sorbitol; mannitol; galacticol; 1,2,6-hexanetriol; non-ionic polyethylene glycol having a molecular weight of from 100 to 800; the propylene and di-propylene gycols; the pentitols such as arabitol; and, mixtures thereof; however, glycerine is preferred.

If the emulsifier/dispersant content is below about 7.5%, the formulation becomes unstable due to lack of iodine complexing capability, and if the emulsifier/dispersant content is above about 12.5%, no significant improvement was observed.

Using an AKYPO™RLM-100 emulsifier/dispersant of about 10%; an $I_2$ content of about 1.05%; an I- content of about 0.28%; about 10% glycerin; citric acid to buffer the pH; caustic to obtain a pH range of about 4.8–5.2; and the balance water (all parts by weight), a suitable formulation was produced having a phase-stable shelf life of about two (2) years within an ambient temperature range of about 30° F.–110° F.

EXAMPLE 1

Using the above formulation, several herds totalling 2,600 dairy cows was treated during a four month period with about 625,000 teat dips. The herd initially had a low mastitis and infection rate, and use of the above formulation neither improved or worsened the condition of the herd. However, there was a significant improvement in teat appearance, such as a smoother teat, with significantly fewer cracks and a consequent lessened opportunity for the spread of infectious disease such as mastitis. Also there was noted a greater improvement in faster let down and onset of milking, indicating lessened irritation of the cow teats.

The life span of cows varies from about three to seven years, and during the period from the commencement of the four month tests in 1988 to 1994, no significant change in the life span of these herds was observed.

EXAMPLE 2

In a more recent 1994 test, 12 dairy herds of about 200 cows each were treated with the above formulation, and a noticeable improvement in teat condition was observed within about ten (10) days. Fewer cracks, sores, callousing, etc., appeared, resulting in the cow teats being much easier to prepare for milking and a consequent faster milking operation due to less discomfort.

Also, there was no increase in the somatic (white cell) count from solutions taken from the teat area, an increase in this cell count being the first sign of a reduced resistance to infectious disease such as mastitis. Additionally, there was a decreased reaction of milker's hands such as chapping, etc., compared to using the NORFOX NP-9 nonyl phenoxy surfactant.

The teat dip and method of this invention provides a product having good germicidal properties, and which imparts a smoother teat with fewer callouses, roughness, sores and cracking. Use of the formulation thus reduces entry sites for infection and subsequent spreading of disease, such as mastitis and milking is made easier, due to less teat irritation. Moreover, the teat dip formulation of this invention is relatively inexpensive and has a reasonably good shelf life at ambient conditions.

I claim:

1. A teat dip solution consisting of:

a water soluble solution of a non-ionic, laureth (11–16) carboxylic acid having an HLB of about 10–16 about 7.5%–12.5%; an effective amount of an iodophor; glycerin: about 5%–12.5%; a buffer; an agent for adjusting the pH to about 4.0–5.5; and, water: balance all parts by weight; the solution having a phase stable shelf life of up to about two years at ambient temperatures.

2. The solution of claim 1, consisting of:

a water soluble solution of a laureth (11–16) carboxylic acid having an HLB of about 10–16; about 7.5%–12.5%; an $I_2$ content of about 0.45%–1.3%; HI, or equivalent: sufficient to form about 0.25%–0.3% $I^-$; glycerin: about 5%–12.5%; a buffer; caustic for adjusting the solution pH to about 4.0–5.5; and, water: balance, all parts by weight; the solution having a phase stable shelf life of up to about two years at ambient temperatures.

3. The solution of claim 2, in which the laureth (11–16) carboxylic acid has an HLB of about 14.8.

4. The solution of claim 2, in which the buffer is selected from the class consisting of citric acid, lactic acid and mixtures thereof, the solution pH is about 4.8–5.2.

5. The solution of claim 2, including HI, KI, NaI, $CaI_2$, and mixtures thereof, thereby forming an effective amount of $I^-$.

6. The solution of claim 2, containing an hydroxy compound selected from the group consisting of:

glycerine, sorbitol, mannitol, galacticol, the propylene and di-propylene glycols, 1,2,6-hexanetriol, pentitols including arabitol, non-ionic polythelene glycol having a molecular weight of from 100–800, and mixtures thereof.

7. The solution of claim 2, comprising a non-ionic, laureth (11–16) carboxylic acid: about 10%; an $I_2$ content of about 0.25%–0.3%; about 10% glycerin; a pH buffer; caustic to obtain a solution pH range of about 4.0–5.5; and, the balance water, all parts by weight.

8. The solution of claim 7, comprising:

laureth (11–16) carboxylic acid with an HLB of 14.8; an $I^-$ content of about 0.28%; a buffer of citric or lactic acid; and, caustic to adjust the solution pH to about 4.8–5.2.

9. A method of treatment for teats to reduce the spread of infectious disease, by applying to the teat area a solution consisting of:

a water soluble solution of a non-ionic, laureth (11–16) carboxylic acid having an HLB of about 10–16: about 7.55–12.5%; an effective amount of an iodophor; glycerin: about 5%–12.5%; a buffer; a caustic for adjusting the solution pH to about 4.0–5.5; and, water: balance, all parts by weight; the solution having a phase stable shelf life of up to about two years at ambient temperatures.

10. The method of claim 9, in which the solution consists of a laureth (11–16) carboxylic acid having an HLB of about 10–16: about 7.55–12.5%; and 12 content of about 0.45%–1.3%; HI or equivalent: sufficient to form about 0.25%–0.3%$I^-$; glycerin: about 5%–12.5%; a buffer; caustic for adjusting the solution pH to about 4.0–5.5; and, water: balance, all parts by weight.

11. The method of claim 9, in which the laureth (11–16) carboxylic acid has an HLB of about 14.8.

12. The method of claim 9, in which the buffer is selected from the class consisting of citric acid, lactic acid and mixtures thereof, and the solution pH is about 4.8–5.2.

13. The method of claim 9, in which HI, KI, NaI, CaI, and mixtures thereof, are employed to form an effective amount of $I^-$.

14. The method of claim 9, in which the solution contains hydroxy compounds selected from the group consisting of:

glycerine, sorbitol, mannitol, galacticol, the propylene and di-propylene glycols, 1,2,6-hexanetriol, pentitols including arabitol, non-ionic polythelene glycol having a molecular weight of from 100–800, and mixtures thereof.

15. The method of claim 9, in which the solution consists of a non-ionic laureth (11–16) carboxylic acid: about 10%; an $I_2$ content of about 0.25%–3.0%; about 10% glycerin; a pH buffer; caustic to obtain a pH range of about 4.0–5.5; and, the balance water, all parts by weight.

16. The method of claim 9, in which the solution consists of: laureth (11–16) carboxylic acid has an HLB of about 14.8; an $I^-$ content of about 0.28%; a buffer of citric or lactic acid; and caustic to adjust the solution pH to about 4.8–5.2.

17. A teat dip solution consisting of:

a water soluble solution of a non-ionic, laureth (11–16) carboxylic acid having an HLB of about 10–16: about 7.5%–12.5%; an effective amount of stabilized iodine; glycerin: about 5%–12.5%; a buffer; an agent for adjusting the pH to about 4.0–5.5; and water: balance, all parts by weight; the solution having a phase stable shelf life of up to about two years at ambient temperatures.

18. The method of treatment according to claim 9, by applying to the teat area a water soluble solution of a non-ionic, laureth (11–16) carboxylic acid having an HLB of about 10–16: about 7.5%–12.5%; an effective amount of stabilized iodine; glycerin: about 5%–12.5%; a buffer; a caustic for adjusting the solution pH to about 4.0–5.5; and, water: balance, all parts by weight.

19. A teat dip solution consisting of: a water soluble solution of a non-ionic, laureth (11–16) carboxylic acid having an HLB of about 10–16: about 7.5%–12.5%; an effective amount of a complexed iodophor; glycerin, or hydroxy equivalent: About 5%–12.5%; a buffer; an agent for adjusting the pH to about 4.0 to 5.5; and water; balance, all parts by weight; the solution having a phase stable shelf life of up to about two years at ambient temperature; the solution being non-irritating and emollient free; and, inducing an exfoliation of dry teat skin, while preserving and protecting natural emollients and moisture in the teat skin.

20. The solution of claim 19, consisting of: a water soluble solution of a laureth (11–16) carboxylic acid having an HLB of about 10–16: about 7.5%–12.5%, an $I_2$ content of about 0.45%–1.3% HI, or equivalent: sufficient to form at least about 0.25%; glycerin, or hydroxy equivalent: about 5%–12.5%; a buffer; caustic for adjusting the solution pH to about 5%–5; and, water; balance, all parts by weight; the solution having a phase stable shelf life of up to about two years at ambient temperatures; the solution being non-irritating and emollient free; and, inducing an exfoliation of dry teat skin, while preserving and protecting natural emollients and moisture in the teat skin.

21. A teat dip solution consisting of: a water soluble solution of a non-ionic, laureth (11–16) carboxylic acid having an HLB of about 10–16: about 7.5%–12.5%; an effective amount of stabilized iodine; glycerin, or hydroxy equivalent: about 5%–12.5%; a buffer, an agent for adjusting the pH to about 4.0–5.5; and, water; balance, all pads by weight; the solution having a phase stable shelf life of up to about two years at ambient temperatures; the solution being non-irritating and emollient free; and, inducing an exfoliation of dry teat skin, while preserving and protecting natural emollients and moisture in the teat skin.

22. The method of claim 9, consisting of applying to the teat area a water soluble solution of a non-ionic, laureth (11–16) carboxylic acid having a HLB of about 10–16; about 7.5%–12.5%; an effective amount of stabilized iodine; glycerin; about 5%–12.5%; a buffer; a caustic for adjusting the solution pH to about 4.0–5.5; and, water balance; the solution being non-irritating and emollient free; and, inducing an exfoliation of dry teat skin, while preserving and protecting natural emollients and moisture in the teat skin.

* * * * *